United States Patent [19]
Rueter

[11] Patent Number: 5,495,055
[45] Date of Patent: Feb. 27, 1996

[54] ACETONE HYDROGENATION USING A SUPPORTED RUTHENIUM CATALYST

[75] Inventor: Michael A. Rueter, Malvern, Pa.

[73] Assignee: Arco Chemical Technology, L.P., Greenville, Del.

[21] Appl. No.: 388,007

[22] Filed: Feb. 13, 1995

Related U.S. Application Data

[63] Continuation-in-part of Ser. No. 290,327, Aug. 12, 1994.

[51] Int. Cl.⁶ .................. C07C 29/143; C07C 29/145
[52] U.S. Cl. .................. 568/881; 568/876; 568/878; 568/880
[58] Field of Search .................. 568/876, 878, 568/880, 881

[56] References Cited

U.S. PATENT DOCUMENTS

| | | | |
|---|---|---|---|
| 2,871,102 | 1/1959 | Rust et al. | 423/584 |
| 2,871,104 | 1/1959 | Rust | 423/584 |
| 3,766,279 | 10/1973 | Fenton et al. | 568/880 |
| 4,268,454 | 5/1981 | Pez et al. | 568/880 |
| 4,322,315 | 3/1982 | Drake | 252/415 |
| 4,331,557 | 5/1982 | Drake | 252/411 |
| 4,929,776 | 5/1990 | Grosselin et al. | 568/862 |
| 5,384,418 | 1/1995 | Zajaeck et al. | 549/531 |

*Primary Examiner*—Werren B. Lone
*Attorney, Agent, or Firm*—Stephen D. Harper

[57] ABSTRACT

A deactivated supported ruthenium catalyst which has been used to continuously hydrogenate an aqueous acetone stream is regenerated by contacting with steam at an elevated temperature. Periodic regeneration in this manner serves to maintain a high rate of reaction in a process which converts acetone to isopropanol.

14 Claims, 1 Drawing Sheet

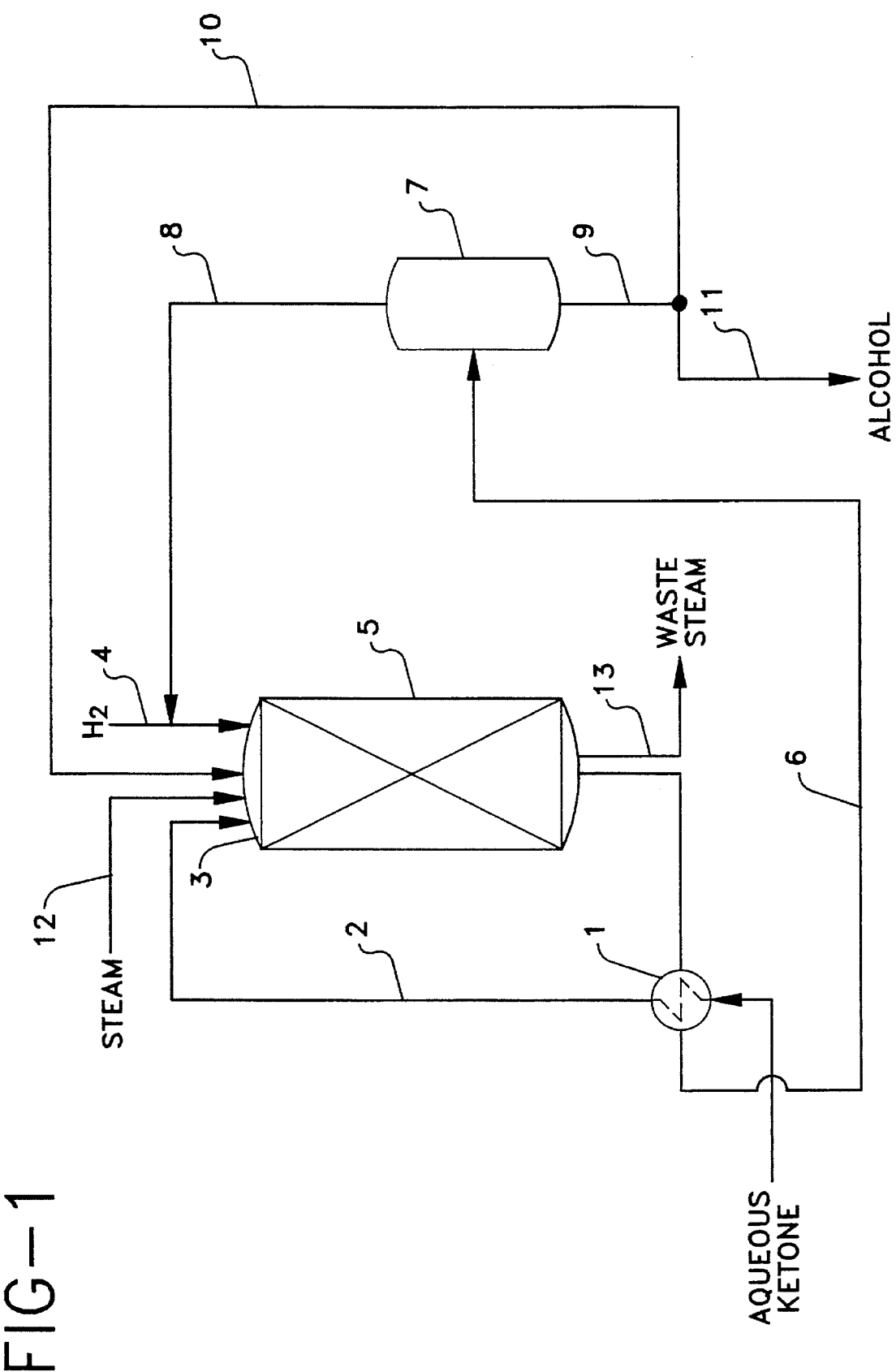

ACETONE HYDROGENATION USING A SUPPORTED RUTHENIUM CATALYST

This is a continuation-in-part of application Ser. No. 08/290,327 filed Aug. 12, 1994.

FIELD OF THE INVENTION

This invention relates to methods whereby the high activity and selectivity of a ruthenium catalyst in a continuous fixed bed acetone hydrogenation process may be advantageously maintained by periodic steaming of the catalyst.

BACKGROUND OF THE INVENTION

Recently, an integrated olefin epoxidation process was proposed wherein a secondary alcohol such as isopropanol is air-oxidized to form an oxidant mixture comprised of acetone, isopropanol, and hydrogen peroxide, the acetone is removed from the oxidant mixture, and the resulting acetone-lean oxidant mixture is used to epoxidize an olefin such as propylene in the presence of a titanium silicalite catalyst (U.S. Pat. No. 5,384,418; incorporated herein by reference in its entirety). The acetone which is removed is recycled back to isopropanol by reacting with hydrogen in the presence of a catalyst. In the past, typical hydrogenation processes have required high pressures, normally above 1200–1500 psig. Substantial savings, particularly with respect to the cost of building commercial scale plants, could be realized if efficient hydrogenation at lower pressures were possible. For example, large capacity compressors are not needed at hydrogenation pressures less than 500 psig. Additionally, low pressure hydrogen streams are commonly available at nominal cost from existing commercial sources (i.e., as by-products of other chemical processes).

Hydrogenation of the ketone removed from the oxidant mixture is complicated by the fact that substantial quantities of water will generally also be present. I have discovered that the use of supported ruthenium catalysts results in initial hydrogenation rates and selectivities to alcohol which are sufficiently high to be commercially useful in hydrogenating aqueous acetone streams of this type. However, after several days of continuous use, the activity of such catalysts decreases to an unacceptable level. As such catalysts are quite expensive, simply replacing the spent catalyst with fresh catalyst is not practical. Moreover, any regeneration technique which requires the catalyst to be removed from the hydrogenation reactor or treated with expensive reagents or requires a series of lengthy steps will also not be attractive from a commercial point of view.

Moreover, the regeneration of hydrogenation catalysts is a highly unpredictable and uncertain art. A standard treatise on hydrogenation [Rylander, *Catalytic Hydrogenation in Organic Syntheses*, Academic Press, p. 4 (1979)] observes that "[i]t is not easy to enumerate catalyst poisons" since "[t]hey vary from reaction to reaction." Further, according to this reference, while "[l]ost catalyst activity can sometimes be restored by regeneration," it is also true that "[o]ne can never be certain in advance which procedures will work." The prior art has previously suggested that ruthenium hydrogenation catalysts could be reactivated by either heating under reduced pressure and thereafter reducing the catalyst (U.S. Pat. No. 4,331,557) or by treating with carbon tetrachloride (U.S. Pat. No. 4,322,315).

SUMMARY OF THE INVENTION

This invention provides an acetone hydrogenation process wherein a supported ruthenium catalyst is periodically regenerated by steaming. It has unexpectedly been discovered that such a regeneration step effectively restores the activity of the catalyst, may be practiced without removing the catalyst from a fixed bed within the hydrogenation reactor, and requires a minimum of reactor downtime.

The invention comprises the steps of feeding an aqueous acetone stream and from 1 to 5 moles of molecular hydrogen per mole of acetone into a reactor having a fixed catalyst bed comprised of an activated supported ruthenium catalyst, maintaining said aqueous stream and molecular hydrogen in the reactor at a temperature of from 75° C. to 180° C. for a time effective to accomplish conversion of at least a portion of the acetone to isopropanol and withdrawing a product stream comprised of water and isopropanol from the reactor. The foregoing steps are continuously performed until such time that the activated supported ruthenium catalyst is transformed to a partially deactivated supported ruthenium catalyst exhibiting an apparent first order rate constant less than 80% of the apparent first order rate constant of the activated supported ruthenium catalyst. The partially deactivated catalyst is then contacted with steam of a temperature of from 100° C. to 200° C. for a time effective to regenerate the activated supported ruthenium catalyst. The regenerated catalyst is thereafter utilized to catalyze the aforedescribed hydrogenation of the aqueous acetone stream.

DETAILED DESCRIPTION OF THE INVENTION

The aqueous acetone stream to be hydrogenated in accordance with the process of this invention is comprised of acetone and at least 5 weight percent water. In one preferred embodiment, however, isopropanol is also present. For example, the aqueous acetone stream may be obtained by removing acetone by a suitable separation means such as distillation from an oxidant mixture comprised of isopropanol, acetone, water, and hydrogen peroxide. The composition of such an aqueous acetone stream typically will be as follows: 10 to 80 weight percent acetone, 15 to 80 weight percent isopropanol and 5 to 15 weight percent water. Minor amounts of other organic species such as esters, acids, and aldehydes may also be present without detrimentally affecting the desired acetone hydrogenation which takes place in the process of this invention.

The aqueous acetone stream is contacted with from 1 to 5 moles of molecular hydrogen ($H_2$) per mole of acetone as it passes through the reactor containing the fixed bed of supported ruthenium catalyst. Use of less than 1 mole of hydrogen will result in incomplete conversion of the acetone, while amounts greater than 5 moles are not necessary and will tend to cause large amounts of isopropanol and acetone to be carried into the vapor phase. Therefore, avoidance of high hydrogen to acetone molar ratios allows post-hydrogenation separation of the unreacted excess hydrogen from the isopropanol product to be more economically accomplished. The range of from 1 to 2 moles of $H_2$ per mole of acetone is particularly advantageous. The pressure maintained during hydrogenation is not critical, but typically is within the range of from 50 to 1000 psig. The optimum pressure will depend upon a number of factors such as the projected total life of the catalyst; in certain embodiments, an operating pressure of from 500 to 800 psig is preferred. In other embodiments, however, such as when the catalyst life is relatively long, the operating pressure is preferably in the range of 200 to 400 psig.

The ruthenium catalysts suitable for regeneration by the process of this invention are supported ruthenium catalysts.

The catalyst support or carrier can be any solid support which does not deleteriously affect the catalytic process. Examples of supports include carbon, kieselguhr, silica, alumina, silica-alumina, calcium carbonate, barium carbonate, pumice, clays, and the like, and mixtures thereof. For reasons of economics, stability, and inertness, the presently preferred support is carbon. The support can be in the form of spheres, pellets, extrudates, tablets, granules, and the like, and mixtures thereof. The size of the catalyst support will be any size suitable for the particular catalytic reaction and equipment. In a fixed bed system, the support advantageously has a particle size larger than 0.5 mm.

The amount of ruthenium present on the support can vary. In general, the supported ruthenium catalyst will contain ruthenium in the range from about 0.01 to about 50 weight percent and preferably in the range of about 0.5 to about 5 weight percent, based on the weight of the support.

The supported ruthenium catalyst can be prepared by any of the methods well-known in the art. The ruthenium catalyst can be added to the support as finely divided elemental ruthenium or compounds of ruthenium which are reducible by hydrogen to finely divided elemental ruthenium. Suitable reducible compounds include ruthenium oxide, ruthenium chloride, ruthenium nitrate, ruthenium acetate, ruthenium carbonate, ruthenium hydroxide, and the like. The ruthenium catalyst can be added to the support by any of a variety of methods. For example, the supported catalysts can be prepared by dry mixing the components or by impregnating the support with a solution or a dispersion of ruthenium in elemental form or in the form of reducible compounds thereof. The supported catalyst can be pretreated with hydrogen to reduce the compounds, or such reduction can be achieved in the hydrogenation reactor. Examples of supported catalysts include 0.5 percent ruthenium on alumina, 1 percent ruthenium on alumina, 10 percent ruthenium on alumina, 5 percent ruthenium on carbon, 15 percent ruthenium on silica, 3 percent ruthenium on keiselguhr, and 6 percent ruthenium on calcium carbonate. Promoters or activators, such as chromium, palladium, silver, manganese, and the like can be present in the supported catalyst if desired.

Suitable supported ruthenium catalyses are also readily available from commercial sources including, for example, the Degussa Corporation and Johnson Mathey Inc. Additional information concerning such catalysts may be found in the following texts: Augustine, *Catalytic Hydrogenation*, Marcel Dekker, New York 1985; Freifelder, *Practical Catalytic Hydrogenation* Wiley-Interscience, New York 1971; Rylander, *Catalytic Hydrogenation Over Platinum Metals*, Academic Press, New York 1967; Rylander, *Hydrogenation Methods*, Academic Press, London 1985.

The supported ruthenium catalyst should be deployed in the reactor in a form capable of being maintained in a fixed bed state so that a suitably high rate of aqueous acetone flow through the reactor and intimate contact between the acetone, hydrogen, and catalyst surface may be attained without loss of the catalyst as the isopropanol product stream is withdrawn.

The aqueous ketone stream and molecular hydrogen may be contacted with the supported ruthenium catalyst at a temperature of from 75° C. to 180° C. Preferably, however, said temperature is from 90° C. to 150° C. since such temperatures generally tend to provide optimum catalyst activity and selectivity.

As a consequence of the hydrogen: acetone ratios and temperatures utilized, the reaction pressure within the reactor will generally be from about 50 to 800 psig in order to maintain the acetone substantially as a liquid phase, with the hydrogen being at least partially dissolved in the liquid phase. Preferred pressures are those which permit at least some vaporization of the liquid phase to take place. Such pressures allow better control of the exotherm which occurs during hydrogenation.

The flow rate of the aqueous acetone stream through the reactor is adjusted in accordance with the quantity of catalyst in the fixed bed within the reactor such that the weight hour space velocity (WHSV) is in the range of 0.1 to 5 kilograms acetone per kilogram catalyst per hour.

Depending upon the scale of the reactor and the hydrogen gas and liquid aqueous acetone feed streams utilized, the fixed bed hydrogenation reactor may operate in a trickle flow, pulsed flow, or bubble flow regime. Generally speaking, improved results will be obtained when the flow pattern is such that the catalyst is fully wetted and all available surface area is utilized. Improved mass transfer, and therefore a higher reaction rate, is favored at higher gas and liquid velocities, which occur in the pulsed and bubble flow regimes. However, such regimes are also characterized by higher pressure drops. The optimum operating conditions may be readily ascertained by routine experimentation.

The reactor may be run using either an upflow or a downflow of the reactants, although the latter is preferred. Upflow of the reactants will tend to result in liquid continuous (bubble) flow, such that the interfacial area for gas-to-liquid transport of the hydrogen is limited. Downflow allows for at least partially gas-continuous flow, even at the relatively high flows which characterize the pulsed flow regime. This increases the interfacial area for hydrogen transport and helps bring the gas phase into more intimate contact with the catalyst surface.

The reactor may be operated with either a concurrent or counter-current flow of reactants. Concurrent flow is preferred, since it helps to avoid the problem of flooding and high pressure drops that can arise with counter-current flow.

BRIEF DESCRIPTION OF DRAWING

The process of this invention may be performed in an apparatus such as that diagrammed schematically in FIG. 1. In the apparatus the aqueous acetone stream that contains the acetone to be hydrogenated is passed through heat exchanger 1 via supply line 2 and then supplied into reactor 3. The aqueous acetone stream will typically be in liquid form when introduced. Reactor 3 may be any suitable size and configuration and may, for example, be in the form of a tank, tube, column, or the like. The diameter of the reactor should preferably be selected to provide the capacity to process ketone at a minimum velocity of 2000 lbs/hr/ft.$^2$ More than one reactor may be operated, either in tandem or in series. The use of two or more reactors in tandem is especially desirable, as the reactors may be alternated between hydrogenation and catalyst regeneration such that isopropanol is produced on a continuous basis. A single reactor may have a plurality of stages, beds, or chambers arranged therein. The hydrogen is passed through supply line 4 into the reactor; a compressor may be utilized to achieve the desired pressure and feed rate. The hydrogen and the aqueous acetone stream are passed through the inside of the reactor 3 so that the acetone and hydrogen react at the fixed catalyst bed 5 to form isopropanol, the contents of the reactor being preferably maintained at a temperature of from 75° C. to 180° C. Greater than 90% (more preferably, at least 95%; most preferably, at least 99%) conversion of the acetone is achieved, accompanied by at least 95% (more preferably, at least 99%; most preferably, at least 99.9%) selectivity to isopropanol. The resulting product stream comprised of unreacted hydrogen (if an excess has been used), isopropanol and water (which may also contain minor amounts of acetone and other organics) is discharged from the reactor, passed through heat exchanger 1, and introduced via line 6 into gas/liquid separator 7. In gas/liquid separator 7, which may be, for example, a flash drum, the product stream is separated into a liquid stream comprised of isopropanol and water and a gas stream comprised of hydrogen. The gas stream may be withdrawn via line 8 and the hydrogen contained therein recycled back to reactor 3 (either directly or by first combining with make-up hydrogen); intermediate purification of the gas stream may also be performed. Alternatively, particularly where a low $H_2$ to acetone ratio has been employed, the gas stream is simply purged or vented. The liquid stream is withdrawn via line 9 and either is used directly as a feed to an isopropanol air oxidation process such as that described in U.S. Pat. Nos. 2,871,102, 2,871,102, and 2,871,104 and British Pat. No. 758,907 and 1,421,299 or is subjected to further fractionation (e.g., distillation) as so to separate the isopropanol from water, ketone, other alcohols, organic acids or esters, or other components of the liquid stream.

In a particularly preferred embodiment of the invention, however, a portion of the product stream (or the liquid stream) is recycled back to the reactor (for example, through line 10) with the remaining portion being removed via line 11. Preferably, from 25% to 90% of the product stream is recycled in this manner. An important advantage of this mode of operation is that the recycled product stream or liquid stream (which contains little, if any, acetone) helps to dilute the aqueous acetone stream. The acetone concentration within the reactor is thereby lowered, making temperature control significantly easier.

When the activity of the supported ruthenium catalyst has decreased to an unacceptable level relative to the activity of said catalyst when freshly prepared, regeneration of the catalyst is preformed by contacting the catalyst with steam. The relative activity of the catalyst may be easily monitored by measurement of the percent conversion of the acetone in the aqueous acetone stream which takes place during a single pass through the fixed bed reactor under constant reaction conditions. Typically, it will be advantageous to conduct such regeneration once the catalyst activity is less than 80% of the original activity (as measured by apparent first order rate constant). Preferably, regeneration is performed before the activity of the catalyst drops to less than 50% of its original value. In general, the process of this invention may be operated for between 100 and 1000 hours before catalyst regeneration becomes desirable. Under certain operating conditions, even longer cycles between catalyst regeneration are possible (e.g., up to 10,000 hours). The catalyst may be subjected to numerous hydrogeneration and regeneration cycles before replacement is necessary, as it has been found that contacting with steam in accordance with the invention permits the catalyst to repeatedly attain an activity comparable to or very nearly that of fresh catalyst.

When catalyst regeneration is performed, the flow of the aqueous acetone stream and molecular hydrogen into the reactor may be discontinued and the residual reactants and products within the reactor withdrawn from the reactor prior to introduction of steam. Regeneration of the partially deactivated supported ruthenium catalyst takes place by passing steam through the fixed bed containing the catalyst. Steam, for example, may be introduced to the reactor through feed line 12 and withdrawn via line 13. In an alternative embodiment of the invention, the source of steam may be the aqueous acetone stream in vapor form since such a vaporized stream will typically contain sufficient water to regenerate the catalyst. This embodiment has several advantages. For example, the amount of process piping would be reduced owing to the elimination of the need for separate steam lines. In addition, draining the liquid contents of the reactor prior to regeneration would not be necessary. While the use of steam alone would produce a waste stream requiring disposal, the vaporized aqueous acetone stream which has been used for regeneration could be condensed and then recycled into the hydrogenation process (a preliminary purification of such a condensed stream may be desirable in order to avoid re-introduction of catalyst poisons into the reactor). The mechanism by which the steam reactivates the used catalyst is not known, although it is believed that perhaps organic impurities on the surface of the catalyst are removed by steaming. The type of steam utilized is not critical; wet steam (containing a relatively high proportion of water), dry steam, saturated steam or superheated steam may all be used to advantage. Other gases such as nitrogen, helium, hydrogen, carbon dioxide, or the like as well as organic compounds in vapor form may be admixed with the steam. The temperature within the fixed bed of the reactor is preferably from 100° C. to 200° C. during steaming; pressures of from 1 to 5 atmospheres are generally suitable. The time required for reactivation will vary depending upon the degree to which the catalyst has been poisoned as well as the temperature, pressure, and rate of steam flow through the fixed bed, but typically from 1 to 24 hours will suffice. After contacting with steam, the regenerated catalyst may be immediately returned to service in the hydrogenation steps of this invention, although under some circumstances pretreatment of the regenerated catalyst with hydrogen alone at a temperature of from 100° C. to 600° C. may be desirable.

EXAMPLE

An aqueous acetone stream containing 30 weight % acetone, 10 weight % water, and 60 weight % isopropanol was passed over a fixed catalyst bed comprised of ruthenium supported on carbon (obtained from Johnson Mathey; Ru content=1 weight %) in concurrent downflow with a hydrogen feed. The weight hour space velocity was 1.5 kilograms acetone per kilogram catalyst per hour and the $H_2$: acetone molar feed ratio was 1.25: 1. The catalyst bed was maintained at an average temperature of 100° C. and a pressure of 300 psig. Initial acetone conversion was greater than 99%, with 99.9% selectivity to isopropanol. After 500 hours of operation, the conversion dipped to 94%. The catalyst bed was then regenerated in situ with steam at 150° C. and 15 psig for 14 hours. When the hydrogenation reaction was restarted using the same conditions as described hereinabove, acetone conversion improved to 96.5%. Operation for another 170 hours caused the acetone conversion to decline to 92%. Another steam treatment at 175° C. and 15 psig restored the acetone conversion to 99%. Operation for another 200 hours caused the acetone conversion to drop to 95%. Another treatment with steam at 175° C. and 15 psig raised the acetone conversion to 98%. This demonstrates the utility of the process of the invention, which is capable of producing isopropanol in high yield from an aqueous acetone stream over a prolonged period of time.

I claim:

1. An acetone hydrogenation process comprising the steps of (a) feeding an aqueous acetone stream and from 1 to 5 moles of molecular hydrogen per mole of acetone into a reactor having a fixed catalyst bed comprised of an activated supported ruthenium catalyst;

(b) maintaining said aqueous acetone stream and molecular hydrogen in the reactor at a temperature of from 75° C. to 180° C. for a time effective to accomplish conversion of at least a portion of the acetone to isopropanol;

(c) withdrawing a product stream comprised of water and isopropanol from the reactor;

(d) continuously performing steps (a), (b), and (c) until such time that the activated supported ruthenium catalyst is transformed to a partially deactivated supported ruthenium catalyst exhibiting an apparent first order rate constant less than 80% of the apparent first order rate constant of the activated supported ruthenium catalyst;

(e) contacting the partially deactivated supported ruthenium catalyst with steam at a temperature of from 100° C. to 200° C. for a time effective to regenerate the activated supported ruthenium catalyst; and (f) repeating steps (a), (b), and (c) using the activated supported ruthenium catalyst obtained by regeneration.

2. The process of claim 1 wherein said activated supported ruthenium catalyst is comprised of a support selected from the group consisting of silica, alumina, carbon, kieselguhr, and calcium carbonate.

3. The process of claim 1 wherein said activated supported ruthenium catalyst is comprised of 0.5 to 5 weight percent ruthenium.

4. The process of claim 1 wherein step (e) is performed at a pressure of from 1 to 5 atmospheres.

5. The process of claim 1 wherein the contacting time in step (e) is from 1 to 24 hours.

6. The process of claim 1 wherein steps (a), (b), and (c) are performed at a weight hourly space velocity of from 0.1 to 5 kilograms acetone per kilogram of activated supported ruthenium catalyst per hour.

7. The process of claim 1 wherein the aqueous acetone stream is additionally comprised of isopropanol.

8. The process of claim 1 wherein at least 90% conversion of the acetone to isopropanol takes place in step (b).

9. The process of claim 1 wherein a portion of the product stream is recycled back to the reactor.

10. The process of claim 9 wherein from 25% to 90% of the product stream is recycled back to the reactor.

11. The process of claim 1 wherein the partially deactivated supported ruthenium catalyst is maintained in the fixed bed of the reactor during step (e).

12. The process of claim 1 wherein the steam in step (e) is provided by vaporizing the aqueous acetone stream.

13. The process of claim 1 wherein the aqueous acetone stream and molecular hydrogen are maintained in the reactor in step (b) at a pressure of 50 to 1000 psig.

14. An acetone hydrogenation process comprising the steps of (a) feeding an aqueous acetone stream comprised of acetone, water, and isopropanol and from 1 to 2 moles of molecular hydrogen per mole of acetone into a reactor having a fixed catalyst bed comprised of an activated supported ruthenium catalyst comprising a carbon support and 0.5 to 5 weight percent ruthenium;

(b) maintaining said aqueous acetone stream and molecular hydrogen in the reactor at a pressure of from 50 to 1000 psig and a temperature of from 90° C. to 150° C. for a time effective for accomplish at least 90% conversion of the acetone to isopropanol;

(c) withdrawing a product stream comprised of water and isopropanol from the reactor;

(d) continuously performing steps (a), (b), and (c) until such time that the activated supported ruthenium catalyst is transformed to a partially deactivated ruthenium catalyst exhibiting an apparent first order rate constant of greater than 50% and less than 80% of the apparent first order rate constant of the activated supported ruthenium catalyst;

(e) passing steam through the fixed bed comprised of the partially deactivated supported ruthenium catalyst at a temperature of from 100° C. to 200° C. and a pressure of from 1 to 5 atmospheres for 1 to 24 hours to regenerate the activated supported ruthenium catalyst; and (f) repeating steps (a), (b), and (c) using the activated supported ruthenium catalyst obtained by regeneration.

\* \* \* \* \*